United States Patent [19]
Frost et al.

[11] Patent Number: 4,583,994
[45] Date of Patent: * Apr. 22, 1986

[54] CYCLIC PROCESS FOR PRODUCING METHANE IN A TUBULAR REACTOR WITH EFFECTIVE HEAT REMOVAL

[75] Inventors: Albert C. Frost, Congers; Chang-Lee Yang, Spring Valley, both of N.Y.

[73] Assignee: Union Carbide Corporation, Danbury, Conn.

[*] Notice: The portion of the term of this patent subsequent to Sep. 28, 1999 has been disclaimed.

[21] Appl. No.: 377,029

[22] Filed: May 11, 1982

Related U.S. Application Data

[62] Division of Ser. No. 158,802, Jun. 12, 1980, Pat. No. 4,351,646.

[51] Int. Cl.[4] .............................................. C10K 3/04
[52] U.S. Cl. ................................. 48/197 R; 585/733
[58] Field of Search .............. 48/197 R; 423/DIG. 6; 585/733

[56] References Cited

U.S. PATENT DOCUMENTS 4,242,103 12/1980 Rabo et al. ...................... 48/197 R
4,351,646 9/1982 Frost et al. ......................... 585/733

OTHER PUBLICATIONS

Hougen et al., "Chemical Process Principles", Part three, pp. 1031–1034, John Wiley & Sons, 1947.

Primary Examiner—Peter Kratz
Attorney, Agent, or Firm—Alvin H. Fritschler

[57] ABSTRACT

Carbon monoxide-containing gas streams are converted to methane by a cyclic, essentially two-step process in which said carbon monoxide is disproportionated to form carbon dioxide and active surface carbon deposited on the surface of a catalyst, and said carbon is reacted with steam to form product methane and by-product carbon dioxide. The exothermic heat of reaction generated in each step is effectively removed during each complete cycle so as to avoid a build up of heat from cycle-to-cycle, with particularly advantageous techniques being employed for fixed bed, tubular and fluidized bed reactor operations.

5 Claims, No Drawings

CYCLIC PROCESS FOR PRODUCING METHANE IN A TUBULAR REACTOR WITH EFFECTIVE HEAT REMOVAL

STATEMENT

The Government of the United States of America has rights pursuant to Contract No. ET-78-C-03-2153 awarded by the Department of Energy.

This application is a division of our prior U.S. Ser. No. 158,802, filed June 12, 1980, now U.S. Pat. No. 4,351,646.

BACKGROUND OF THE INVENTION

1. Field of the Invention

The invention relates to the production of methane from carbon monoxide. More particularly, it relates to a methanation process capable of effectively utilizing carbon monoxide-containing gas streams on a continuous cyclic basis.

2. Description of the Prior Art

It has heretofore been proposed to utilize carbon monoxide present in gas streams, particularly in dilute carbon monoxide-containing waste streams. for the production of methane. This process is uniquely suited for the utilization of carbon monoxide in gas streams not previously suitable as feed streams for the commercial production of methane. In the practice of this process, a carbon monoxide-containing gas stream is passed over a suitable disproportionation catalyst under conditions such that the carbon monoxide is decomposed to form carbon dioxide and active surface carbon, designated as C* and deposited on the catalyst, according to the reaction:

$$2\ CO \rightarrow CO_2 + C^* \tag{1}$$

The carbon dioxide and inert gases present in the feed stream are vented from the surface layer of active surface carbon, which is thereafter converted to methane by contact with steam as follows:

$$2\ C^* + 2H_2O \rightarrow CH_4 + CO_2 \tag{2}$$

Upon separation from the accompanying $CO_2$ by conventional means, methane is recovered in the form of a low-cost, relatively pure product, with the carbon values thus recovered being at least about 12.5 percent and up to nearly 25 percent of the carbon present in the carbon monoxide decomposed upon contact with the catalyst.

The decomposition of carbon monoxide over a disproportionation catalyst, in accordance with reaction (1) above is carried out at a reaction temperature of from about 100° C. to about 350° C., preferably at from about 200° C. to about 300° C. for practical commercial operations. The carbon monoxide-containing gas stream is passed over the catalyst for a time sufficient to deposit a surface layer of active surface carbon on the catalyst essentially without the formation of inactive coke thereon. Such inactive coke is not only itself inert under the methanation conditions of the process, but may tend to reduce the capacity of the catalyst to form active surface carbon in subsequent operations of the cyclic, essentially two-step process.

The active surface carbon deposited on the catalyst, following the venting of inert gases therefrom, is contacted with steam or a steam-containing gas stream to convert said active surface carbon to methane and carbon dioxide in accordance with reaction (2) above. Reaction temperatures of from about 100° C. to about 400° C. may be employed, with temperatures of from about 200° C. to about 350° C. being generally preferred.

With respect to this known process, it is understood that said CO disproportionation temperature refers to the average temperature of the reaction bed and that the particular reaction temperature pertaining to any given commercial application will be subject to inevitable variations depending on the type of operation employed, e.g., fixed, tubular or fluidized bed, and on the capability of temperature control equipment employed in such applications. While the disproportionation reaction temperature may exceed the indicated temperature limits on a transitory basis, the economic and technical practicality of commercial applications of the process are enhanced when the preferred temperature limits are observed. At higher temperatures, the suitability of the catalyst for use in the cyclic two-step process is diminished so that the overall efficiency of the process is adversely effected. The cost of the methane is thereby increased at such less favorable operating conditions.

Both reaction steps (1) and (2) are exothermic. If the process is carried out on a cyclic basis, therefore, a steady build up of heat from cycle to cycle is possible, requiring disruption of the operation for cooling to maintain operating conditions with the preferred limits indicated above. Such a disruption is undesirable, of course, and would contribute adversely to the feasibility of employing the process in practical commercial applications. It is highly desirable in the art that processing techniques be developed to enable the cyclic, two-step process to be carried out in such practical commercial applications without disruption resulting from the build up of heat from cycle to cycle because of the exothermic nature of each of the major processing steps of the process.

It is an object of the invention, therefore, to provide an improved process for the production of methane.

It is another object of the invention to provide a process for the low-cost production of methane from carbon monoxide-containing gas streams in practical commercial operations.

It is a further object of the invention to provide a process for the catalytic production of methane from carbon monoxide-containing gas streams on a cyclic, essentially two-step basis without disruption due to the build up of heat from cycle to cycle.

With these and other objects in mind, the invention is hereinafter described in detail, the novel features thereof being particularly pointed out in the appended claims.

SUMMARY OF THE INVENTION

Each step of the cyclic, two-step methanation process is carried out in a manner such that the exothermic heat of reaction generated during each step is removed from the catalyst bed essentially prior to the exposure of the catalyst bed, or portion thereof, to the exothermic heat of reaction of the next succeeding step of the process such that operations are maintained in a temperature range of from about 230° C. and about 310° C. Essentially complete removal of all of the heat generated during each complete cycle is thereby achieved. The exothermic reaction steps of (1) disproportionation of the carbon monoxide content of a feed gas stream to form active surface carbon, and (2) the reaction of said carbon with steam to form methane, can thus be carried out on a cyclic basis without a steady build-up of heat from cycle to cycle. Operations are carried out in an adiabatic fixed bed reactor employing a feed gas stream having a CO concentration of less than about 1.9 percent by volume, commonly less than about 1.4 percent by volume. Operations in a tubular reactor are advantageously carried out at a CO concentration of at least about 25 percent by volume, commonly at least about 4.3 percent by volume, with the exothermic heat of reaction of each step being dissipated in each portion of the bed through the tube walls to a cooling medium prior to contact of that portion of the bed with the heat front of the next succeeding step. In fluidized bed operations, CO concentrations of from about 1 percent to about 80 percent by volume are employed, with the fluidized bed being collapsed during each steaming step and re-fluidized during the next disproportionation step. Boiler tubes submerged within the fluidized bed effectively remove the exothermic heat of reaction of the disproportionation step and that stored in the bed during the preceding steaming step. Each embodiment of the invention thus avoids the accumulation of heat over the course of consecutive processing cycles, enabling practical commercial operations to be carried out on a continuous basis.

DETAILED DESCRIPTION OF THE INVENTION

The practice of the invention enables the advantageous two-step process to which it relates to be carried out on a continuous cyclic basis in the practical, commercial production of methane from carbon monoxide-containing gas streams. The invention thus serves to enhance the feasibility of employing said cyclic, two-step process for the production of methane from gas streams not previously suitable as feed streams for the commercial practice of methane. The steady build up of heat due to the exothermic nature of the two principal reaction steps of the process is avoided by particular operating techniques, as herein disclosed and claimed, with respect to various reactor configurations conveniently employed in particular embodiments of the process. Because of the limitations on the temperature control equipment employed in practical commercial applications of the process and the inevitable variations resulting from the use of various reactor configurations, reaction temperatures may exceed the preferred temperature limits not only on a transitory basis but as a result of the steady build up of heat from cycle to cycle in continuous processing operations carried out on a commercial scale in the absence of techniques such as those employed in the various embodiments of the invention.

The cyclic, two-step process for the production of methane from carbon monoxide-containing gas streams, to which the present invention relates, is disclosed and claimed in U.S. Pat. No. 4,242,103. It will be appreciated by those skilled in the art that various aspects of the present invention pertain to said cyclic, two-step process, per se, and do not form an essential part of the point of novelty of the invention. The disclosure of the earlier application is incorporated herein by reference, and various features of the cyclic, two-step process, including pertinent information concerning the disproportionation catalysts and compositions, operating pressures and the like, are not repeated herein except to the extent that they may relate specifically to the improved processing techniques herein disclosed and claimed.

It is necessary for the economic and technical practicality of the process that the reaction temperatures be maintained within the preferred temperature limits thereof, although higher temperatures may be tolerated on a transitory basis within the overall scope of the process. Specifically, with respect to practical commercial applications, it has been determined that the disproportionation reaction is advantageously carried out by employing an initial feed gas at a temperature on the order of about 230° C.-240° C. and an desirable upper operating temperature on the order of about 300° C.-310° C., i.e. with a temperature rise due to the exothermic heat of reaction being limited to less than about 80° C. More specifically, it has been determined that the exothermic heat of reaction generated during the disproportionation and steaming steps can be conveniently removed from the catalyst bed, or each portion thereof, essentially prior to the exposure of the catalyst bed, or said portions thereof, to the exothermic heat of reaction of the next succeeding step of the cyclic process such that said essential steps are carried out between an initiation temperature as low as on the order of said 230° C. and said upper operating temperature on the order of about 310° C. In the practice of the invention. essentially complete removal of all of the heat generated during each complete cycle is achieved. Accordingly, the exothermic reaction steps can be carried out on a cyclic basis in practical commercial apparatus without a steady build up of heat from cycle to cycle. Such a heat build up would necessarily result in a disruption of the continuous cyclic processing, adversely effecting the effectiveness and efficiency of the methanation process. Such effects will be appreciated as discussed below with respect to practical reactor configurations useful in the practice of the invention.

In embodiments of the invention utilizing an adiabatic fixed bed reactor, the temperature rise during the disproportionation step is found to be a function of the CO concentration of the feed gas. At a CO concentration of less than about 1.9 percent by volume, the temperature rise will be less than about 80° C., whereas higher concentrations will result in a higher temperature rise in such fixed bed reactors. Furthermore, it has been found that heat front generated by the exothermic heat of the disproportionation reaction will travel through the catalyst bed at a considerably faster rate than the slower moving reaction/cool front travels when the CO concentration is in this low range. Thus, the introduction of a feed gas at an initiation temperature as low as on the order of about 230° C. and with a CO concentration of about 1.9 percent by volume will cause a heat front of up to about 310° C. to travel ahead of the combined reaction/cooling front in which the cooling effect results from the continued introduction of feed gas at said initiation temperature. At the end of the disproportionation step, therefore, i.e. when the disproportionation reaction/cooling front has reached the discharge end of the reactor, most of the bed will have been cooled to as low as about 230° C.

During the following steaming step, the reaction/heating step is found to travel ahead of the lagging cooling front. Consequently, an introduction of steam on the order of about 230° C., with an estimated 80° C. temperature rise, will cause a 310° C. steaming reaction/heating front to travel ahead of the trailing 230° C. cooling front. At the end of this steaming step, therefore, most of the bed will be found to be at a temperature on the order of about 310° C. This stored sensible heat, rather than contributing to a steady build up of heat in the reactor, is, however, quickly incorporated into the fast moving heat front of the next succeeding disproportionation step that travels ahead of the disproportionation reaction/cooling front as indicated above. The stored sensible heat of the steaming step is thus swept from the bed, and the bed temperature never exceeds about 310° C. No accumulation of heat occurs, therefore, over the course of consecutive processing cycles during continuous operation of the cyclic, essentially two-step process. It should be noted that the results indicated above pertain at a carbon loading of about 0.5 weight percent active surface carbon deposition per weight of catalyst composition. Such loadings have been obtained With fresh catalyst, but, in practice, the carbon loading will be found to decline over the course of repeated cyclic operations. Thus, the loadings achieve will decline to 0.4, 0.3 and eventually to about 0.2 weight percent loading at which point further operation without catalyst regeneration becomes uneconomical. The cyclic operation in the reactor will be interrupted at this point for catalyst regeneration after which the cyclic, essentially two-step process will be resumed in that reactor. The decline in carbon loading of the catalyst has been found to cause a shift in the CO concentration that can be employed while remaining within the desirable temperature rise limitation resulting from the exothermic heat of reaction of the disproportionation step. At a carbon loading of 0.3 weight percent, for example, the CO concentration must be less than about 1.40 percent by volume to achieve the desired limitation of the temperature rise to less than about 80° C. At a 0.2 weight percent loading, the CO concentration must be less than about 1.05 percent for volume to achieve said temperature limitation.

In applications in whioh the feed stream contains more than about 1.9 volume percent CO, the adiabatic fixed bed reactor would be employed within the scope of the present invention by diluting the feed stream to less than about 1.9 percent by volume CO. This is conveniently accomplished by recycling cooled effluent from the disproportionation step. Feed streams suitable for use in such applications will commonly contain from about 5 percent to about 70 percent by volume carbon monoxide although feed streams having CO concentrations outside this range can also obviously be accommodated. It will be understood from the above that, as the carbon loading of the catalyst declines, the feed stream, if not already sufficiently dilute, will be diluted by inert gas, e.g. recycle effluent gas from the disproportionation step, to ensure that the CO concentration is within the limits that will ensure that the temperature rise is within the desired limits thereof. Thus, at a carbon loading of about 0.3 weight percent, the feed stream will be diluted, as required, to less than about 1.40 percent. At a 0.2 carbon loading, dilution would be to less than about 1.05 percent by volume.

In embodiments of the invention utilizing a catalyst-containing tubular reactor, feed streams having an appropriate CO concentration can be treated without the need for the recycle referred to with respect to adiabatic fixed bed reactors. It will be understood that, in this reactor configuration, the catalyst will commonly be packed within many parallel reaction tubes surrounded by a cooling medium, e.g. boiling water or boiling dowtherm, although the catalyst may also be packed on the shell side of the reactor with the cooling medium in the tubes. The heat of reaction of both the disproportionation and the steaming steps is dissipated radially through the reactor walls to the cooling medium. At a CO concentration of at least about 25 percent by volume, the temperature rise will be less than about 80° C., whereas lower concentrations will result in a higher temperature rise in such tubular reactors.

At such higher CO concentrations, the disproportionation reaction/heating front resulting from the exothermic heat of reaction travels through the reactor at a faster rate than the slower moving cooling front, with the reaction heat thereby being temporarily stored in the catalyst-containing tubular reactor. The resulting higher temperature of the catalyst provides the driving force to dissipate heat through the walls of the tubes to the cooling medium, which is provided in sufficient quantity to remove said heat. At the end of the disproportionation step, therefore, the inlet end of the catalyst bed will have been cooled to the initiation temperature of the feed gas, i.e. to as low as on the order of about 230° C., prior to the commencement of the steaming step. The middle portion of the catalyst bed will have been cooled to an intermediate temperature, and the effluent end of the catalyst bed will be at its highest temperature, but not exceeding the upper desired temperature limit of about 310° C. The catalyst just in front of the reaction/heating front of the steaming step will have just cooled down, therefore, so that the steaming reaction/heating front continually approaches cooled catalyst, with the heat of reaction of the steaming step being temporarily stored in the catalyst bed. The resulting higher temperature of the catalyst will provide the driving force to dissipate heat through the walls of the tubes to the cooling medium. The next succeeding disproportionation reaction/heating front thus approaches catalyst that has just cooled down so that said front approaches cooled catalyst. The accumulation of heat over the course of consecutive processing cycles is thereby avoided by the rippling of disproportionation and steaming fronts down the length of the tubular reactor.

It should be noted that the results indicated above pertain to a carbon loading of about 0.5 weight percent active surface carbon deposition per weight of catalyst composition. As the loading decreases to about 0.3, it has been determined that the CO concentration can be reduced, with the desired operation referred to above pertaining to feed streams having a CO concentration of at least about 4.3 percent by volume. At a carbon loading of about 0.2, the CO concentration can be at least about 2.1 percent by volume while achieving said rippling of the heat fronts through the reactor to avoid the accumulation of heat from cycle to cycle. When the feed gas contains CO in a concentration of less than the amounts indicated herein, the tubular reactor configuration would not be applicable for the treatment of such feed streams within the preferred limits of temperature increase herein disclosed.

In embodiments of the invention utilizing a fluidized bed reactor, feed gas is passed to the fluidized bed for the disproportionation step, after which the bed is collapsed to a packed bed during the steaming step in which the amount of steam employed is considerably less than the amount of feed gas employed in the disproportionation step. The carbon monoxide-containing feed gas stream is passed to the reactor at an initiation temperature as low as on the order of about 230° C. and at a CO concentration of from about 1 percent to about 80 percent by volume. Unlike the fixed bed reactor and tubular reactor embodiments, the fluidized bed reactor thus may be employed to recover methane from any practical CO-containing waste stream available from a variety of processing operations. Those skilled in the art will appreciate that more concentrated CO-continuing streams can usually be processed advantageously by conventional means.

The exothermic heat of reaction generated during the disproportionation step is removed, in the practice of the invention, from the reactor through boiler tubes submerged within the reactor without a temperature rise within the fluidized bed. The boiler tubes, however, effectively serve only to partially remove the exothermic heat of reaction during the subsequent steaming step in which the bed is collapsed about said tubes. During the steaming step, the steaming reaction/heating front moves through the bed faster than the slower moving cooling front. As a result, the temperature of the bed is raised from the initiation temperature, i.e. as low as on the order of about 230° C., to an upper temperature not exceeding on the order of about 310° C. The sensible heat thus stored in the bed during the steaming step is removed during the next succeeding disproportionation step, said submerged boiler tubes being adapted, by the size thereof and the cooling medium and temperature employed, to effectively dissipate said stored heat upon fluidization of the bed. The temperature of the bed is thus reduced, during the next disproportionation step, from the highest temperature not exceeding about 310° C. to the initiation temperature, i.e. as low as on the order of about 230° C. By such cyclic operation utilizing a fluidized bed for disproportionation and a collapsed bed for steaming, the accumulation of heat is effectively avoided over the course of consecutive processing cycles. The use of a fluidized bed reactor configuration in this embodiment of the invention is particularly advantageous in the treatment of feed streams, such as waste streams, containing from about 5 percent to about 50 percent by volume carbon monoxide.

Those skilled in the art will appreciate that the various embodiments of the invention can be carried out using any suitable disproportionation catalyst, as discussed in the reference incorporated herein as indicated above. It will be understood that nickel is the preferred catalyst and, as employed, is present in its metal state apart from small amounts of oxidation that may occur in the course of the processing operations. It will be also understood that, upon separation from by-product carbon dioxide formed during reaction (2) the methane is obtained as a relatively pure product. In those circumstances in which it is desired to ensure the high purity of the methane product, by-product carbon dioxide can be recycled to the catalyst bed upon completion of the disproportionation step, said carbon dioxide serves to purge the bed and thus displace residual feed gas remaining in the void spaces of the catalyst bed. This supplemental recycle step may advantageously be employed in the fixed bed, tubular reactor or fluidized bed embodiments of the invention, if so desired. With respect to the adiabatic fixed bed embodiment, the pressure workload and the size of the compressors required for the primary feed stream and for the recycle stream can be significantly reduced by employing the catalyst in the bed in the form of monolithic blocks having numerous straight channels that offer negligible resistance to the flow of gas therethrough.

Those skilled in the art will appreciate that, in another embodiment, the disproportionation step could be followed by a purge step to remove the exothermic heat of reaction prior to the beginning of the steaming step. Such a purge would likewise be employed following the steaming step to remove the exothermic heat of reaction generated during this step. Such a disproportionation-purge-steaming-purge cycle, while not departing essentially from the two-step nature of the cyclic process will be seen to be less desirable than the embodiments discussed above. It will be noted that such a cycle necessarily involves the use of two purge steps in addition to the two principal steps of the process to avoid the accumulation of heat over the course of consecutive processing cycles. By contrast, the adiabatic fixed bed reactor embodiment discussed above utilizes the heat front generated by the disproportionation reaction to sweep the stored sensible heat from the steaming reaction from the bed along with the rapidly traveling heat front itself. This accomplishes the purging action in a single operation inherent to the process under the conditions recited, avoiding the need for employing two separate purge steps in each cycle. At relatively high CO concentrations, the double purge embodiment becomes more economical than when utilizing more dilute CO-containing streams. At typical carbon loadings, e.g., at the 0.5 percent carbon loading referred to above, the double purge embodiment results in temperature increases considerably above up to about 80° C. rise referred to above with respect to practical commercial operations. For these reasons, the disproportionation-purge-steaming-purge cycle is less desirable and useful than the advantageous fixed bed, tubular reactor and fluidized bed embodiments that conveniently serve to avoid the accumulation of heat in practical cycle to cycle operations on an economically feasible commercial scale.

The invention has herein been described with reference to an initiation temperature as low as on the order of about 230° C., an upper temperature not exceeding on the order of about 310° C., with the temperature rise thus being limited in each cycle to less than about 80° C. An initiation temperature of about 230°-240° C. has been found generally desirable for effective carrying out of the processing steps. An upper temperature limitation of about 300°-310° C. is generally desirable to provide assurance, in operations carried out in commercial scale equipment, that the exothermic reaction steps will readily be maintained within the generally preferred temperature range for the process. Those skilled in the art will appreciate, however, that the temperature rise of each reaction step can exceed said limit of about 80° C. while the process is maintained within the generally preferred limits of from about 200° C. to about 350° C. heretofore determined apart from the build-up of heat that would need to be avoided in commercial operations. Thus, one could operate the process with an initiation temperature as low as about 200° C. although an initiation temperature of about 230° C. or 240° C. is generally more advantageous. In accordance with the present invention, the CO concentrations and the other features, such as the cooling medium conditions in the tubular reactor case or the submerged boiler tubes in the fluidized bed case, can be adapted to limit the temperature rise to less than about 80° C., e.g. a desirable 60° C. rise, or, alternately, such features can be adapted to allow the temperature rise to result in an upper temperature up to but not exceeding on the order of about 310° C. It is for purposes of establishing such flexibility in temperature, and in the scope of the present invention, that the term "on the order of about" has been used herein. As used, this term will be understood to denote the reasonable scope to which the invention should reasonably be entitled while carrying out the overall exothermic reactions in practical commercial equipment within the generally preferred limits and avoiding the steady build up of heat from cycle to cycle that would lead to premature disruption of the processing operations. It will also be understood that the various reactor configuration embodiments can be carried out without the necessity for utilizing the limits of the temperature rise, or reasonable extensions thereof indicated herein. In the fixed bed embodiment, for example, the CO concentration should be less than about 1.66 percent by volume at 0.5 percent carbon loading, and less than about 1.26 percent by volume at a 0.3 percent carbon loading, to limit the temperature rise to about 60° C. With the catalyst compositions presently available, carbon loadings have been limited to about 0.5 weight percent for fresh or freshly regenerated catalyst. It will be appreciated that subsequent catalyst development may enable higher carbon loadings, e.g. 1.0 weight percent to be achieved. Such higher carbon loadings are desirable with respect to the overall economic feasibility of the process. Such higher carbon loadings would, however, shift the heat profiles resulting in the faster and slower traveling fronts that are taken advantage of in the practice of the embodiments herein disclosed and claimed. For example, a fixed bed embodiment at a 1.0 weight percent loading would be expected to result in a temperature rise of about 60° C. when the CO concentration is maintained at about 2.17 percent by volume, while for the same fixed bed and temperature rise using fresh catalyst presently available at a carbon loading of 0.5 weight percent, the CO concentration should be less than about 1.66 percent by volume. At a 0.3 weight percent carbon loading at a further point in the overall operation, the CO concentration would have to be maintained at less than about 1.26 percent by volume to limit the temperature rise to said 60° C. From such examples, those skilled in the art will readily appreciate that routine adjustments can be made to accommodate different desired temperature rises, initiation temperatures feed stream concentrations, and achievable carbon loadings within the scope of the particular processing techniques disclosed with reference to the various embodiments of the invention. For the tubular and fluidized bed reactors, such adjustments can be readily made, as by boiler-tube diameter or coolant temperature variations, to accommodate such processing variations within the scope of the invention. In all such embodiments and variations, the invention enables the cyclic, essentially two-step process to be effectively carried out while avoiding the accumulation of heat over the course of consecutive and repeated processing cycles.

It will be appreciated that various changes and modifications can be made in the details of the process without departing from the scope of the invention as disclosed and claimed. For example, the process will commonly be carried out in more than one reactor, with each reactor being cycled between the disproportionation step and the steaming step. For continuous operation, one bed may thus be in the disproportionation step while the second bed is on the steaming step. In a three bed system, the third bed may be withdrawn from production for regeneration while the continuous processing operations are continued, on a cyclic basis, in the other two beds. In this regard, it will be noted that while the steaming step can generally tolerate a higher upper temperature in the generally preferred ranges heretofore determined for the process. i.e. up to about 400° C. continuous cyclic operations between reaction beds requires that the exothermic heat of reaction of the steaming step be dissipated within the time and temperature constraints of the disproportionation step to avoid a steady build up of heat during continuous processing operations in which a bed completing its steaming step is to be contacted with additional feed gas for disproportionation as continuous cyclic operations are continued.

In an illustrative example of the practice of the invention, an adiabatic fixed bed reactor is loaded with a nickel-zirconia coprecipitated catalyst having a weight ratio of 9 parts of nickel per part of zirconia support additive, said nickel being in metal form. The catalyst composition is mixed with a boehmite alumina, i.e. aluminum oxo-hydroxide, binder in a weight ratio of 4 parts of said catalyst composition to 1 part of binder. Upon mixing, the catalyst composition-binding agent paste is peptized in $HNO_3$, extruded and fired in air at 300° C., and reduced and stabilized by being heated at 250° C. for 16 hours in a 10/1 helium/hydrogen mixture. A feed stream having about 25 percent CO is passed to the reactor at an initiation temperature of 230° C. said feed stream being mixed with recycle carbon dioxide in sufficient quantity to reduce the CO concentration to about 1.9 percent by volume prior to entering the reactor. At said CO concentration and using said fresh catalyst with which carbon loadings of about 0.5 weight percent are achieved, the temperature rise due to the exothermic heat of reaction will raise the temperature of the catalyst to less than about 80° C. The heat front will travel, at the diluted CO concentration indicated, through the catalyst bed ahead of the disproportionation reaction/cooling front, thus raising the bed temperature to about 310° C. The inlet end of the bed, and succeeding portions of the bed, will nevertheless be cooled by said reaction/cooling front to said initiation temperature prior to the commencement of the steaming step. The exothermic heat of reaction of the steaming step will result in a reaction/heating front that travels through the bed faster than the trailing cooling front so that sensible heat is left behind and stored during the steaming step. The heat front generated upon the introduction of feed gas at the initiation temperature during the next disproportionation step, introduced without regeneration of the catalyst following said initial processing cycle, serves to incorporate said sensible heat therein and purge this heat remaining from the steaming step from the bed in advance of the trailing disproportionation reaction/cooling front. All of the exothermic heat of reaction is thus removed so that no accumulation of heat from cycle to cycle occurs. As the carbon loading of the catalyst declines, the CO concentration of the feed gas-recycle gas mixture passed to the reactor must likewise be lowered to maintain the temperature rise to said value of less than about 80° C. over the course of the continuous processing operations. For this purpose, more recycle gas is conveniently mixed with the feed gas to dilute the CO concentration of the mixture, with the CO concentration being not more than about 1.40 percent by volume when the carbon loading has decline to about 0.3 weight percent. In other examples, the CO concentration would, of course, be maintained at a lower CO concentration throughout although the use of higher CO concentration streams is obviously desirable from an economic viewpoint.

Using the same catalyst composition packed in the tubes of a tubular reactor and with the same desired initiation temperature of about 230° C. and the same desired temperature rise limitation of not more than about 80° C., the feed gas having a CO concentration of about 25 percent would not need to be diluted as in the adiabatic fixed bed reactor example. At said concentration and at the carbon loadings typically achieved, the reaction/heating fronts for both the disproportionation and the steaming steps travel through the tubular reactor at a faster rate than the trailing cooling fronts. Boiling water is provided as the cooling medium on the shell side of the reactor to remove the heat dissipated through the walls of the reactor tubes to the cooling medium. Thus, the bed is cooled following each reaction step such that each succeeding reaction/heat front contacts catalyst that has been cooled down by such heat dissipation through the walls of the reactor tubes. The reaction/heat fronts thus ripple down the length of the reactor, from the inlet end to the discharge end thereof, without the accumulation of heat from cycle to cycle. The indicated feed stream is likewise treated in a fluidized bed reactor without dilution. Boiler tubes submerged in the fluidized bed serve to remove the exothermic heat of reaction of the disproportionation step so that the bed is at about the initiation temperature upon completion of this step, collapse of the bed and the carrying out of the steaming step. As the boiler tubes are not fully effective in removing the heat when the bed is in the collapsed state about said boiler tubes, the steaming reaction/cooling front moves through the collapsed, i.e. packed, bed faster than the cooling front, with sensible heat thus being stored in the bed and raising the temperature up to about 310° C. by the end of the steaming step. During the next succeeding disproportionation step, the submerged boiler tubes are again fully effective to remove the heat from the bed upon the fluidization thereof. The boiler tubes are adapted to effectively dissipate said stored heat from the steaming step as well as the heat generated during the disproportionation step. As a result, the temperature of the bed is reduced to about 230° C. during the disproportionation step so that the next steaming step commences with the bed back at its initiation temperature. No heat accumulates, therefore, over the course of consecutive processing cycles.

The cyclic, essentially two-step process to which the present invention relates provides for the production of methane from heretofore unsuitable sources of CO, such as the effluent from blast furnace operations, underground coal gasification, the raw synthesis gas from the oxygen-blown gasification of coal and the like. In turn, the process enables CO-containing gas streams, frequently discharged as waste streams from such processing operations, to be effectively utilized for a desirable purpose rather than being flared or otherwise disposed of as unsuited for use in conventional methanation techniques or for other purposes. The invention enhances the technical and economic feasibility of said cyclic process by providing means to avoid the steady build up of heat from cycle to cycle in practical commercial operations. The invention thus serves to facilitate consideration of the use of the subject cyclic process for the production of high purity methane as a replacement for natural gas. This constitutes an important advance in the continuing effort to meet the energy requirements of industrial societies throughout the world.

What is claimed is:

1. In a cyclic, essentially two-step process for the production of methane from carbon-monoxide-containing gas streams by (a) disproportionation of the carbon monoxide at a temperature of about 100°–350° C. in a catalyst-containing reactor to form carbon monoxide and an active surface carbon that is deposited on the surface of the disproportionation catalyst essentially without the formation of inactive coke thereon, (b) reaction of said active surface carbon with steam at about 100°–400° C. to form methane and carbon dioxide, and (c) passing additional carbon monoxide-containing gas over said catalyst from step (b) and repeating said steps (a) and (b) a cyclic basis, the improvement comprising removing the exothermic heat of reaction generated during each of said steps (a) and (b) from the catalyst bed, or a portion thereof essentially prior to the exposure of the catalyst bed, or said portion thereof, to the exothermic heat of reaction of the next succeeding step of the cyclic process such that said steps (a) and (b) are carried out between an initation temperature as low as on the order of about 230° C. and an upper temperature not exceeding on the order of about 310° C. with the essentially complete removal of all of the heat generated during each complete cycle, with said steps (a) and (b) being carried out in a catalyst-packed tubular reactor containing a cooling medium, and including passing the carbon monoxide-containing feed gas stream to said tubular reactor at an initiation temperature as low as on the order of about 230° C. and at a CO concentration of at least about 2.1 percent by volume, the temperature rise during the disproportionation step thereby being limited to less than about 80° C. and the reaction/heating front resulting from the exothermic heat of reaction traveling through the reactor tubes at a faster rate than the slower moving cooling front, with the disproportionation reaction heat front thereby being temporarily stored in the catalyst-containing tubular reactor, with the resulting higher temperature of the catalyst providing the driving force to dissipate heat through the walls of the tubes to said cooling medium provided in sufficient quantity to remove said heat, so that, at the end of disproportionation step (a), the inlet end of the catalyst bed has been cooled as low as the initiation temperature range prior to the commencement of step (b), the middle portion of the bed has been cooled to an intermediate temperature, and the effluent end of the catalyst bed is at the highest temperature but not exceeding said upper temperature of about 310° C., the catalyst just in front of the reaction/heating front of steaming step (b) having just been cooled down so that said steaming reaction/heating front continually approaches cooled catalyst, with the steaming reaction heat being temporarily stored in the catalyst-containing bed, with the resulting higher temperature of the catalyst providing the driving force to dissipate heat through the walls of the tubes to the cooling medium, the next succeeding disproportionation reaction/heating front thus approaching catalyst that has just cooled down so that said front approaches cooled catalyst, thereby avoiding the accumulation of heat over the course of consecutive processing cycles by the rippling of disproportionation and steaming fronts down the length of said reactor.

2. The process of claim 1 in which said feed gas stream has a CO concentration of at least about 25 percent by volume.

3. The process in claim 1 in which said disproportionation catalyst comprises nickel present in its metal state.

4. The process of claim 1 in which said feed gas stream has a CO concentration of at least about 4.3 percent by volume.

5. The process of claim 1 and including recycling by-product carbon dioxide to the tubular reactor upon completion of the disproportionation step, said carbon dioxide serving to purge the bed, thus displacing residual feed gas remaining in the void spaces of the catalyst and ensuring a high purity methane product.

* * * * *